(12) United States Patent
Yoshida et al.

(10) Patent No.: US 9,284,354 B2
(45) Date of Patent: *Mar. 15, 2016

(54) IMMUNOGLOBULIN-BINDING POLYPEPTIDE

(75) Inventors: Shinichi Yoshida, Takasago (JP); Dai Murata, Takasago (JP); Shunichi Taira, Takasago (JP)

(73) Assignee: Kaneka Corporation, Osaka (JP)

(*) Notice: Subject to any disclaimer, the term of this patent is extended or adjusted under 35 U.S.C. 154(b) by 51 days.

This patent is subject to a terminal disclaimer.

(21) Appl. No.: 14/007,211

(22) PCT Filed: Mar. 26, 2012

(86) PCT No.: PCT/JP2012/057799
§ 371 (c)(1),
(2), (4) Date: Dec. 16, 2013

(87) PCT Pub. No.: WO2012/133342
PCT Pub. Date: Oct. 4, 2012

(65) Prior Publication Data
US 2014/0100356 A1    Apr. 10, 2014

(30) Foreign Application Priority Data
Mar. 25, 2011  (JP) ................. 2011-068497

(51) Int. Cl.
*C07K 14/00* (2006.01)
*C07K 14/47* (2006.01)
*C07K 14/31* (2006.01)

(52) U.S. Cl.
CPC ................. *C07K 14/00* (2013.01); *C07K 14/31* (2013.01); *C07K 14/47* (2013.01)

(58) Field of Classification Search
CPC ......... C07K 14/00; C07K 14/47; C07K 14/31
See application file for complete search history.

(56) References Cited

U.S. PATENT DOCUMENTS

| 5,143,844 | A | 9/1992 | Abrahmsen et al. |
| 6,831,161 | B1 | 12/2004 | Uhlén et al. |
| 2010/0286373 | A1* | 11/2010 | Majima et al. ............. 530/387.2 |
| 2012/0208234 | A1 | 8/2012 | Yoshida et al. |
| 2013/0096276 | A1 | 4/2013 | Yoshida et al. |
| 2014/0005357 | A1 | 1/2014 | Nakamura et al. |

FOREIGN PATENT DOCUMENTS

| CN | 1642976 A | 7/2005 |
| JP | 62-190087 | 8/1987 |
| JP | 2002-527107 A | 8/2002 |
| JP | 2005-538693 A | 12/2005 |
| JP | 2006-304633 A | 11/2006 |
| JP | 2008-115151 A | 5/2008 |
| JP | 2010-504754 A | 2/2010 |
| WO | WO-2010/110288 A1 | 9/2010 |
| WO | WO-2011/077395 A1 | 6/2011 |
| WO | WO-2011118699 A1 | 9/2011 |
| WO | WO-2012086660 A1 | 6/2012 |

OTHER PUBLICATIONS

Linhult, M., et al., "Improving the Tolerance of a Protein A Analogue to Repeated Alkaline Exposures Using a Bypass Mutagenesis Approach", *Proteins: Structures, Function and Bioinformation*, 2004, vol. 55, No. 2, pp. 407-416.
Yoshida, S., et al., "Rational design and engineering of protein A to obtain the controlled elution profile in monoclonal antibody purification", *Chem-Bio Informatics Journal*, 2012, vol. 12, pp. 1-13.
Palmer, B., et al., "Design of stability at extreme alkaline pH in streptococcal protein G", *Journal of Biotechnology*, 2008, vol. 134, pp. 222-230.
Gulich, S., et al., "Engineering streptococcal protein G for increased alkaline stability", *Protein Engineering*, 2002, vol. 15, No. 10, pp. 835-842. Abstract Only.
International Preliminary Report on Patentability issued in PCT/JP2012/057799, Oct. 2, 2013. English translation.

* cited by examiner

*Primary Examiner* — James H Alstrum Acevedo
*Assistant Examiner* — Erinne Dabkowski
(74) *Attorney, Agent, or Firm* — Novak Druce Connolly Bove + Quigg LLP

(57) ABSTRACT

An object of the present invention is to provide novel polypeptides that are capable of binding to an immunoglobulin and have high stability against alkali. The present invention relates to proteins having the amino acid sequence of SEQ ID No:1 or 2.

4 Claims, 2 Drawing Sheets

SEQUENCE LISTING

```
<160> NUMBER OF SEQ ID NOS: 48

<210> SEQ ID NO 1
<211> LENGTH: 58
<212> TYPE: PRT
<213> ORGANISM: Artificial Sequence
<220> FEATURE:
<223> OTHER INFORMATION: Novel polypeptide (Artificial)

<400> SEQUENCE: 1

Ala Asp Asn Arg Phe Asn Arg Glu Gln Gln Asn Ala Phe Tyr Glu Ile
1               5                   10                  15
```

```
Leu His Leu Pro Asn Leu Thr Glu Glu Gln Arg Asn Ala Phe Ile Gln
        20                  25                  30

Ser Leu Arg Asp Asp Pro Ser Val Ser Arg Glu Ile Leu Ala Glu Ala
            35                  40                  45

Arg Arg Leu Asn Asp Ala Gln Ala Pro Gly
        50                  55

<210> SEQ ID NO 2
<211> LENGTH: 58
<212> TYPE: PRT
<213> ORGANISM: Artificial Sequence
<220> FEATURE:
<223> OTHER INFORMATION: Novel polipeptide (Artificial)

<400> SEQUENCE: 2

Ala Asp Asn Arg Phe Asn Arg Glu Gln Gln Asn Ala Phe Tyr Glu Ile
1               5                   10                  15

Leu His Leu Pro Asn Leu Thr Glu Gln Arg Asn Ala Phe Ile Gln
        20                  25                  30

Ser Leu Arg Asp Asp Pro Ser Val Ser Arg Glu Ile Leu Ala Glu Ala
            35                  40                  45

Arg Arg Leu Asn Asp Ala Gln Ala Pro Arg
        50                  55

<210> SEQ ID NO 3
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 3
cgtggatccg cagacaaccg tttcaaccgg gaacaacaaa atgctttcta tgaaattta      60 catttaccta ac                                                        72

<210> SEQ ID NO 4
<211> LENGTH: 72
<212> TYPE: DNA
<213> ORGANISM: Artificial Sequence
<220> FEATURE:
<223> OTHER INFORMATION: synthetic oligonucleotide

<400> SEQUENCE: 4
gcgcaagctt tggatgaagg cgttacgttg ttcttcagtt aagttaggta aatgtaaaat      60
ttcatagaaa gc                                                          72

<210> SEQ ID NO 5
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 5
caaagcttgc gcgacgatcc ttcagtgagc cgcgaaattt agcagaagc tcggcgccta      60

<210> SEQ ID NO 6
<211> LENGTH: 57
<212> TYPE: DNA
<213> ORGANISM: Artificial Sequence
<220> FEATURE:
<223> OTHER INFORMATION: synthetic oligonucleotide
```

```
<400> SEQUENCE: 6
cgatgaattc tattttggtg cttgagcatc gtttaggcgc cgagcttctg ctaaaat      57

<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 7
cgtggatctg cagacaac                                                 18

<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 8
gaattctatt tggcccctgg tgc                                           23

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gctttcgggg ccgacaaccg                                               20

<210> SEQ ID NO 10
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 10
cacgatgaat tctatttgga tcctggtgct tgag                               34

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
gaattctatt ttgctcgagg tgcttg                                        26

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 12
atggcttctc gagcagacaa ccg                                           23

<210> SEQ ID NO 13
<211> LENGTH: 116
```

```
<212> TYPE: PRT
<213> ORGANISM: Artificial Sequence
<220> FEATURE:
<223> OTHER INFORMATION: Novel polypeptide (Artificial)

<400> SEQUENCE: 13

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Gly Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 14
<211> LENGTH: 116
<212> TYPE: PRT
<213> ORGANISM: Artificial Sequence
<220> FEATURE:
<223> OTHER INFORMATION: Novel polypeptide (Artificial)

<400> SEQUENCE: 14

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 15
<211> LENGTH: 116
<212> TYPE: PRT
<213> ORGANISM: Artificial Sequence
<220> FEATURE:
<223> OTHER INFORMATION: Published polypeptide (mutant)

<400> SEQUENCE: 15

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
```

```
              20                  25                  30
Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
 50                  55                  60

Lys Glu Gln Gln Asn Ala Phe Tyr Glu Ile Leu His Leu Pro Asn Leu
 65                  70                  75                  80

Thr Glu Glu Gln Arg Asn Ala Phe Ile Gln Ser Leu Lys Asp Asp Pro
                 85                  90                  95

Ser Val Ser Lys Glu Ile Leu Ala Glu Ala Lys Lys Leu Asn Asp Ala
                100                 105                 110

Gln Ala Pro Lys
        115

<210> SEQ ID NO 16
<211> LENGTH: 21
<212> TYPE: DNA
<213> ORGANISM: Artificial Sequence
<220> FEATURE:
<223> OTHER INFORMATION: oligonucleotide

<400> SEQUENCE: 16
gcagaagctc agcgcctaaa c                                           21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide

<400> SEQUENCE: 17
gtttaggcgc tgagcttctg c                                           21

<210> SEQ ID NO 18
<211> LENGTH: 24
<212> TYPE: DNA
<213> ORGANISM: Artificial Sequence
<220> FEATURE:
<223> OTHER INFORMATION: oligonucleotide

<400> SEQUENCE: 18
ccttcatcca aatcttgcgc gacg                                        24

<210> SEQ ID NO 19
<211> LENGTH: 24
<212> TYPE: DNA
<213> ORGANISM: Artificial Sequence
<220> FEATURE:
<223> OTHER INFORMATION: oligonucleotide

<400> SEQUENCE: 19
cgtcgcgcaa gatttggatg aagg                                        24

<210> SEQ ID NO 20
<211> LENGTH: 24
<212> TYPE: DNA
<213> ORGANISM: Artificial Sequence
<220> FEATURE:
<223> OTHER INFORMATION: oligonucleotide

<400> SEQUENCE: 20
ccttcatcca acacttgcgc gacg                                        24
```

```
<210> SEQ ID NO 21
<211> LENGTH: 24
<212> TYPE: DNA
<213> ORGANISM: Artificial Sequence
<220> FEATURE:
<223> OTHER INFORMATION: oligonucleotide

<400> SEQUENCE: 21
cgtcgcgcaa gtgttggatg aagg                                              24

<210> SEQ ID NO 22
<211> LENGTH: 22
<212> TYPE: DNA
<213> ORGANISM: Artificial Sequence
<220> FEATURE:
<223> OTHER INFORMATION: oligonucleotide

<400> SEQUENCE: 22
cttcatccaa gagttgcgcg ac                                                22

<210> SEQ ID NO 23
<211> LENGTH: 22
<212> TYPE: DNA
<213> ORGANISM: Artificial Sequence
<220> FEATURE:
<223> OTHER INFORMATION: oligonucleotide

<400> SEQUENCE: 23
gtcgcgcaac tcttggatga ag                                                22

<210> SEQ ID NO 24
<211> LENGTH: 22
<212> TYPE: DNA
<213> ORGANISM: Artificial Sequence
<220> FEATURE:
<223> OTHER INFORMATION: oligonucleotide

<400> SEQUENCE: 24
cttcatccaa ctgttgcgcg ac                                                22

<210> SEQ ID NO 25
<211> LENGTH: 22
<212> TYPE: DNA
<213> ORGANISM: Artificial Sequence
<220> FEATURE:
<223> OTHER INFORMATION: oligonucleotide

<400> SEQUENCE: 25
gtcgcgcaac agttggatga ag                                                22

<210> SEQ ID NO 26
<211> LENGTH: 22
<212> TYPE: DNA
<213> ORGANISM: Artificial Sequence
<220> FEATURE:
<223> OTHER INFORMATION: oligonucleotide

<400> SEQUENCE: 26
cttcatccaa acgttgcgcg ac                                                22

<210> SEQ ID NO 27
<211> LENGTH: 22
<212> TYPE: DNA
<213> ORGANISM: Artificial Sequence
<220> FEATURE:
```

<223> OTHER INFORMATION: oligonucleotide

<400> SEQUENCE: 27
gtcgcgcaac gtttggatga ag        22

<210> SEQ ID NO 28
<211> LENGTH: 21
<212> TYPE: DNA
<213> ORGANISM: Artificial Sequence
<220> FEATURE:
<223> OTHER INFORMATION: oligonucleotide

<400> SEQUENCE: 28
gcttgcgcat cgatccttca g        21

<210> SEQ ID NO 29
<211> LENGTH: 21
<212> TYPE: DNA
<213> ORGANISM: Artificial Sequence
<220> FEATURE:
<223> OTHER INFORMATION: oligonucleotide

<400> SEQUENCE: 29
ctgaaggatc gatgcgcaag c        21

<210> SEQ ID NO 30
<211> LENGTH: 58
<212> TYPE: PRT
<213> ORGANISM: Artificial Sequence
<220> FEATURE:
<223> OTHER INFORMATION: Novel polypeptide (artificial)

<400> SEQUENCE: 30

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Arg
    50                  55

<210> SEQ ID NO 31
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 31

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Gln Arg Leu Asn Asp Ala Gln Ala Pro Arg
    50                  55

<210> SEQ ID NO 32
<211> LENGTH: 58
<212> TYPE: PRT
<213> ORGANISM: Artificial Sequence

```
<220> FEATURE:
<223> OTHER INFORMATION: novel polypeptide (artificial)

<400> SEQUENCE: 32

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Arg Arg Leu Asn Asp Ala Gln Ala Pro Arg
    50                  55

<210> SEQ ID NO 33
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 33

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Arg Arg Leu Asn Asp Ala Gln Ala Pro Arg
    50                  55

<210> SEQ ID NO 34
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 34

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Arg Asp Asp Pro Ser Val Ser Arg Glu Ile Leu Ala Glu Ala
        35                  40                  45

Arg Arg Leu Asn Asp Ala Gln Ala Pro Arg
    50                  55

<210> SEQ ID NO 35
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 35

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45
```

```
Arg Arg Leu Asn Asp Ala Gln Ala Pro Arg
        50                  55

<210> SEQ ID NO 36
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 36

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Thr Leu Arg Asp Asp Pro Ser Val Ser Arg Glu Ile Leu Ala Glu Ala
        35                  40                  45

Arg Arg Leu Asn Asp Ala Gln Ala Pro Arg
        50                  55

<210> SEQ ID NO 37
<211> LENGTH: 58
<212> TYPE: PRT
<213> ORGANISM: Artificial Sequence
<220> FEATURE:
<223> OTHER INFORMATION: novel polypeptide (artificial)

<400> SEQUENCE: 37

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Ile Asp Pro Ser Val Ser Arg Glu Ile Leu Ala Glu Ala
        35                  40                  45

Arg Arg Leu Asn Asp Ala Gln Ala Pro Arg
        50                  55

<210> SEQ ID NO 38
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 38

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
        50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Arg Glu Ile Leu Ala Glu Ala Gln Arg Leu Asn Asp Ala
            100                 105                 110
```

Gln Ala Pro Lys
        115

<210> SEQ ID NO 39
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 39

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Gln Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Ile Asp Asp Pro
                85                  90                  95

Ser Val Ser Arg Glu Ile Leu Ala Glu Ala Gln Arg Leu Asn Asp Ala
            100                 105                 110

Gln Ala Pro Lys
        115

<210> SEQ ID NO 40
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 40

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Ile Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Ile Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 41
<211> LENGTH: 116
<212> TYPE: PRT
<213> ORGANISM: Artificial Sequence
<220> FEATURE:
<223> OTHER INFORMATION: novel polypeptide (artificial)

```
<400> SEQUENCE: 41

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu His Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu His Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 42
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 42

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Arg Asp Asp Pro Ser Val Ser Arg Glu Ile Leu Ala Glu Ala
        35                  40                  45

Arg Arg Leu Asn Asp Ala Gln Ala Pro Arg Ala Asp Asn Arg Phe Asn
    50                  55                  60

Arg Glu Gln Gln Asn Ala Phe Tyr Glu Ile Leu His Leu Pro Asn Leu
65                  70                  75                  80

Thr Glu Glu Gln Arg Asn Ala Phe Ile Glu Leu Arg Asp Asp Pro
                85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 43
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 43

Ala Asp Asn Arg Phe Asn Arg Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Leu Leu Arg Asp Asp Pro Ser Val Ser Arg Glu Ile Leu Ala Glu Ala
        35                  40                  45
```

```
Arg Arg Leu Asn Asp Ala Gln Ala Pro Arg Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Leu Leu Arg Asp Asp Pro
                 85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 44
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 44

Ala Asp Asn Arg Phe Asn Arg Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Thr Leu Arg Asp Asp Pro Ser Val Ser Arg Glu Ile Leu Ala Glu Ala
         35                  40                  45

Arg Arg Leu Asn Asp Ala Gln Ala Pro Arg Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Thr Leu Arg Asp Asp Pro
                 85                  90                  95

Ser Val Ser Arg Glu Ile Leu Ala Glu Ala Arg Arg Leu Asn Asp Ala
            100                 105                 110

Gln Ala Pro Lys
        115

<210> SEQ ID NO 45
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 45

Ala Asp Asn Arg Phe Asn Arg Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Arg Ile Asp Pro Ser Val Ser Arg Glu Ile Leu Ala Glu Ala
         35                  40                  45

Arg Arg Leu Asn Asp Ala Gln Ala Pro Arg Ala Asp Asn Arg Phe Asn
 50                  55                  60

Arg Glu Gln Gln Asn Ala Phe Tyr Glu Ile Leu His Leu Pro Asn Leu
 65                  70                  75                  80

Thr Glu Glu Gln Arg Asn Ala Phe Ile Gln Ser Leu Arg Ile Asp Pro
                 85                  90                  95

Ser Val Ser Arg Glu Ile Leu Ala Glu Ala Arg Arg Leu Asn Asp Ala
            100                 105                 110
```

Gln Ala Pro Lys
        115

<210> SEQ ID NO 46
<211> LENGTH: 116
<212> TYPE: PRT
<213> ORGANISM: Artificial Sequence
<220> FEATURE:
<223> OTHER INFORMATION: novel polypeptide (artificial)

<400> SEQUENCE: 46

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Glu Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Glu Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys
        115

<210> SEQ ID NO 47
<211> LENGTH: 55
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: D, E, N, or Q
<220> FEATURE:
<221> NAME/KEY: MISC_FEATURE
<222> LOCATION: (4)..(4)
<223> OTHER INFORMATION: E or R
<220> FEATURE:
<221> NAME/KEY: MISC_FEATURE
<222> LOCATION: (16)..(16)
<223> OTHER INFORMATION: L, M, or I
<220> FEATURE:
<221> NAME/KEY: MISC_FEATURE
<222> LOCATION: (26)..(26)
<223> OTHER INFORMATION: A, E, F, R, Y, or W
<220> FEATURE:
<221> NAME/KEY: MISC_FEATURE
<222> LOCATION: (30)..(30)
<223> OTHER INFORMATION: D, E, H, I, L, Q, R, S, T, or V
<220> FEATURE:
<221> NAME/KEY: MISC_FEATURE
<222> LOCATION: (32)..(32)
<223> OTHER INFORMATION: H, I, or R
<220> FEATURE:
<221> NAME/KEY: MISC_FEATURE
<222> LOCATION: (33)..(33)
<223> OTHER INFORMATION: D, I, or R
<220> FEATURE:
<221> NAME/KEY: MISC_FEATURE
<222> LOCATION: (34)..(34)
<223> OTHER INFORMATION: D or E
<220> FEATURE:
<221> NAME/KEY: MISC_FEATURE

```
<222> LOCATION: (41)..(41)
<223> OTHER INFORMATION: I, L, or V
<220> FEATURE:
<221> NAME/KEY: MISC_FEATURE
<222> LOCATION: (46)..(46)
<223> OTHER INFORMATION: R or Q
<220> FEATURE:
<221> NAME/KEY: MISC_FEATURE
<222> LOCATION: (47)..(47)
<223> OTHER INFORMATION: H or R
<220> FEATURE:
<221> NAME/KEY: MISC_FEATURE
<222> LOCATION: (55)..(55)
<223> OTHER INFORMATION: R, G, or K

<400> SEQUENCE: 47

Arg Phe Xaa Xaa Glu Gln Gln Asn Ala Phe Tyr Glu Ile Leu His Xaa
1               5                   10                  15

Pro Asn Leu Thr Glu Glu Gln Arg Asn Xaa Phe Ile Gln Xaa Leu Xaa
            20                  25                  30

Xaa Xaa Pro Ser Val Ser Arg Glu Xaa Leu Ala Glu Ala Xaa Xaa Leu
        35                  40                  45

Asn Asp Ala Gln Ala Pro Xaa
    50                  55

<210> SEQ ID NO 48
<211> LENGTH: 58
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(3)
<223> OTHER INFORMATION: Each independently A, D, E, G, H, I, L, N, Q,
      R, S, T, V, or Y
<220> FEATURE:
<221> NAME/KEY: MISC_FEATURE
<222> LOCATION: (6)..(6)
<223> OTHER INFORMATION: D, E, N, or Q
<220> FEATURE:
<221> NAME/KEY: MISC_FEATURE
<222> LOCATION: (7)..(7)
<223> OTHER INFORMATION: E or R
<220> FEATURE:
<221> NAME/KEY: MISC_FEATURE
<222> LOCATION: (19)..(19)
<223> OTHER INFORMATION: L, M, or I
<220> FEATURE:
<221> NAME/KEY: MISC_FEATURE
<222> LOCATION: (29)..(29)
<223> OTHER INFORMATION: A, E, F, R, Y, or W
<220> FEATURE:
<221> NAME/KEY: MISC_FEATURE
<222> LOCATION: (33)..(33)
<223> OTHER INFORMATION: D, E, H, I, L, Q, R, S, T, or V
<220> FEATURE:
<221> NAME/KEY: MISC_FEATURE
<222> LOCATION: (35)..(35)
<223> OTHER INFORMATION: H, I, or R
<220> FEATURE:
<221> NAME/KEY: MISC_FEATURE
<222> LOCATION: (36)..(36)
<223> OTHER INFORMATION: D, I, or R
<220> FEATURE:
<221> NAME/KEY: MISC_FEATURE
<222> LOCATION: (37)..(37)
<223> OTHER INFORMATION: D or E
<220> FEATURE:
<221> NAME/KEY: MISC_FEATURE
<222> LOCATION: (44)..(44)
<223> OTHER INFORMATION: I, L, or V
<220> FEATURE:
<221> NAME/KEY: MISC_FEATURE
```

-continued

```
<222> LOCATION: (49)..(49)
<223> OTHER INFORMATION: R or Q
<220> FEATURE:
<221> NAME/KEY: MISC_FEATURE
<222> LOCATION: (50)..(50)
<223> OTHER INFORMATION: H or R
<220> FEATURE:
<221> NAME/KEY: MISC_FEATURE
<222> LOCATION: (58)..(58)
<223> OTHER INFORMATION: R, G, or K

<400> SEQUENCE: 48

Xaa Xaa Xaa Arg Phe Xaa Xaa Glu Gln Gln Asn Ala Phe Tyr Glu Ile
 1               5                  10                  15

Leu His Xaa Pro Asn Leu Thr Glu Glu Gln Arg Asn Xaa Phe Ile Gln
             20                  25                  30

Xaa Leu Xaa Xaa Xaa Pro Ser Val Ser Arg Glu Xaa Leu Ala Glu Ala
         35                  40                  45

Xaa Xaa Leu Asn Asp Ala Gln Ala Pro Xaa
     50                  55
```

IMMUNOGLOBULIN-BINDING POLYPEPTIDE

CROSS REFERENCE TO RELATED APPLICATIONS

This application is a National Phase filing under 35 U.S.C. §371 of PCT/JP2012/057799 filed on Mar. 26, 2012; and this application claims priority to Application No. 2011-068497 filed in Japan on Mar. 25, 2011, under 35 U.S.C. §119; the entire contents of all are hereby incorporated by reference.

TECHNICAL FIELD

The present invention relates to novel polypeptides having high chemical stability and capable of binding to immunoglobulins.

BACKGROUND ART

Antibodies are capable of specifically binding to substances called antigens, and detoxifying and removing antigen-containing factors with the cooperation of other biomolecules or cells. The name "antibody" is particularly based on such a capability of binding to an antigen, and is also referred to as "immunoglobulin" as a chemical name.

Substances (ligands) capable of specifically binding to constant regions (regions other than antigen-binding sites) of antibodies can be used to purify or detect antibodies. Their ability to bind to constant regions enables them to be used for extended applications, and therefore their industrial importance is sufficiently high. As typical examples of ligands capable of specifically binding to constant regions of antibodies, there may be mentioned Protein A and Protein G.

The development of antibody-related industries such as antibody drugs and laboratory diagnosis has increased the demand for more chemically stable ligands. In particular, there is a strong demand for ligands that are highly stable against alkali because alkalis are used in the deactivation of viruses or the like, or in the washing of carriers (e.g. beads or chips) with immobilized ligands. Since polypeptide ligands are generally vulnerable to alkali attack, many studies have been performed to improve their alkali resistance while maintaining their excellent binding specificity (Non Patent Literatures 1 and 2).

Examples of techniques for improving the alkali resistance of a ligand that binds to an antibody include techniques of mutating Gly at position 29 of Protein A to provide alkali resistance (Patent Literatures 1 and 2); techniques of replacing Asn with another amino acid to provide alkali resistance (Patent Literatures 3 and 4); and techniques using C domain of Protein A or a variant thereof (Patent Literatures 5 and 6).

CITATION LIST

Patent Literature

Patent Literature 1: JP S62-190087 A
Patent Literature 2: WO 2010/110288
Patent Literature 3: JP 2002-527107 T
Patent Literature 4: JP 2005-538693 T
Patent Literature 5: JP 2006-304633 A
Patent Literature 6: JP 2010-504754 T

Non Patent Literature

Non Patent Literature 1: Linhult M. et al., "PROTEINS: Structure, Function, and Bioinformatics", 2004, Vol. 55, pp. 407-416
Non Patent Literature 2: Palmer B. et al., "Journal of Biotechnology", 2008, Vol. 134, pp. 222-230

SUMMARY OF INVENTION

Technical Problem

An object of the present invention is to provide novel polypeptides that are capable of binding to immunoglobulins and have high stability against alkali.

Solution to Problem

In order to achieve the above object, the present inventors used computational chemistry techniques and protein engineering techniques, and finally invented novel polypeptides that differ in sequence from conventionally developed polypeptides, and have much better alkali resistance than such polypeptides.

Specifically, the present invention relates to a polypeptide capable of binding to a protein containing an Fc region of an immunoglobulin, the polypeptide containing the following amino acid sequence:

$RFX_1X_2EQQNAFYEILHX_3PNLTEEQRNX_4FIQX_5LX_6X_7X_8PSVSREX_9LAEAX_{10}X_{11}LNDAQAPX_{12}$ wherein $X_1$ is D, E, N, or Q;
$X_2$ is E or R;
$X_3$ is L, M, or I;
$X_4$ is A, E, F, R, Y, or W;
$X_5$ is D, E, H, I, L, Q, R, S, T, or V;
$X_6$ is H, I, or R;
$X_7$ is D, I, or R;
$X_8$ is D or E;
$X_9$ is I, L, or V;
$X_{10}$ is R or Q;
$X_{11}$ is H or R; and
$X_{12}$ is R, G, or K.

The present invention also relates to a polypeptide capable of binding to a protein containing an Fc region of an immunoglobulin, the polypeptide containing the following amino acid sequence:

$Z_1Z_2Z_3RFX_1X_2EQQNAFYEILHX_3PNLTEEQRNX_4FIQX_5LX_6X_7X_8PSVSREX_9LAEAX_{10}X_{11}LNDAQAPX_{12}$ wherein $X_1$ is D, E, N, or Q;
$X_2$ is E or R;
$X_3$ is L, M, or I;
$X_4$ is A, E, F, R, Y, or W;
$X_5$ is D, E, H, I, L, Q, R, S, T, or V;
$X_6$ is H, I, or R;
$X_7$ is D, I, or R;
$X_8$ is D or E;
$X_9$ is I, L, or V;
$X_{10}$ is R or Q;
$X_{11}$ is H or R;
$X_{12}$ is R, G, or K; and
$Z_1$ to $Z_3$ are each independently A, D, E, G, H, I, L, N, Q, R, S, T, V, or Y.

Preferably, the polypeptide has at least 90% sequence identity to one of the following amino acid sequences:

(SEQ ID No: 1)
ADNRFNREQQNAFYEILHLPNLTEEQRNAFIQSLRDDPSVSREILAEAR

RLNDAQAPG
and (SEQ ID No: 2)
ADNRFNREQQNAFYEILHLPNLTEEQRNAFIQSLRDDPSVSREILAEAR

RLNDAQAPR.

Advantageous Effects of Invention

The polypeptides of the present invention are characterized by their high stability, in particular, against alkali. Even when exposed to very severe alkali conditions (e.g. 0.1 to 1.0 M sodium hydroxide (NaOH)) at room temperature for several hours, the polypeptides hardly lose their ability to bind to immunoglobulins at all.

Many Protein A variants that are engineered to have high alkali resistance without losing the ability to bind to immunoglobulins have already been known. The present invention provides novel peptides that have significantly higher alkali resistance than these variants.

Generally, proteins are extensively cleaved and/or modified when exposed to alkali conditions for a long time. Thus, when the alkali-treated proteins are analyzed with, for example, SDS-PAGE for protein identification, they are less likely to maintain the same band patterns (density, position, and number) as those obtained before the alkali treatment. In contrast, the novel peptides of the present invention, even when exposed to severe alkali conditions, can maintain the same band patterns as before the alkali treatment, and can withstand severer conditions than known alkali-resistant Protein A variants can.

DESCRIPTION OF EMBODIMENTS

Figure 1:
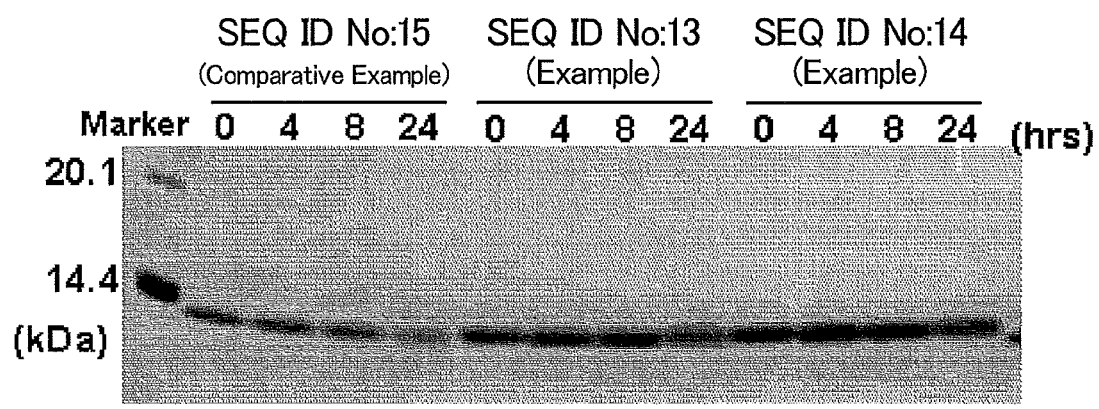
FIG. 1 shows the results of Example 3 and Comparative Example 1, specifically the results of SDS-PAGE on polypeptides of SEQ ID Nos:13 to 15 after exposed to an alkali treatment (for 0, 4, 8, and 24 hours).

The term "polypeptide" used herein is intended to include any molecules of polypeptide structure. The polypeptides of the present invention each contain about 50 amino acid residues, and may thus be generally called "proteins" or "(protein) domains", which are basically intended to be synonymous with "polypeptides".

The expression "protein containing an Fc region of an immunoglobulin" is intended to include immunoglobulin molecules, fragments of immunoglobulins, and derivatives of immunoglobulins. The term "immunoglobulin G derivative" herein is a generic name of modified artificial proteins such as chimeric immunoglobulin Gs in which partial domains of human IgG are substituted and fused with IgG domains of different species, humanized immunoglobulin Gs in which CDRs (Complementarity Determining Regions) of human IgG are substituted and fused with antibody CDRs of different species, immunoglobulin Gs whose Fc region has a molecularly modified sugar chain, and artificial immunoglobulin Gs in which the Fv region and the Fc region of human IgG are fused. It is possible to further modify (e.g. fragmentize) these proteins while maintaining the conformation of the Fc region. Accordingly, the expression "protein containing an Fc region of an immunoglobulin" herein is not limited only to immunoglobulin molecules containing the whole of the region generally called "Fc region" and derivatives thereof.

The novel polypeptides of the present invention are characterized by the ability to bind to a protein containing an Fc region of an immunoglobulin and also by containing the following amino acid sequence:

(SEQ ID NO: 47)
RFX$_1$X$_2$EQQNAFYEILHX$_3$PNLTEEQRNX$_4$FIQX$_5$LX$_6$X$_7$X$_8$PSVSREX$_9$LA

EAX$_{10}$X$_{11}$LNDAQAPX$_{12}$ wherein X$_1$ is D, E, N, or Q;
X$_2$ is E or R;
X$_3$ is L, M, or I;
X$_4$ is A, E, F, R, Y, or W;
X$_5$ is D, E, H, I, L, Q, R, S, T, or V;
X$_6$ is H, I, or R;
X$_7$ is D, I, or R;
X$_8$ is D or E;
X$_9$ is I, L, or V;
X$_{10}$ is R or Q;
X$_{11}$ is H or R; and
X$_{12}$ is R, G, or K.

Preferred are polypeptides that are characterized by binding to a protein containing an Fc region of an immunoglobulin and also by containing the following amino acid sequence:

(SEQ ID NO: 48)
Z$_1$Z$_2$Z$_3$RFX$_1$X$_2$EQQNAFYEILHX$_3$PNLTEEQRNX$_4$FIQX$_5$LX$_6$X$_7$X$_8$PSVS

REX$_9$LAEAX$_{10}$X$_{11}$LNDAQAPX$_{12}$ wherein X$_1$ is D, E, N, or Q;
X$_2$ is E or R;
X$_3$ is L, M, or I;
X$_4$ is A, E, F, R, Y, or W;
X$_5$ is D, E, H, I, L, Q, R, S, T, or V;
X$_6$ is H, I, or R;
X$_7$ is D, I, or R;
X$_8$ is D or E;
X$_9$ is I, L, or V;
X$_{10}$ is R or Q;
X$_{11}$ is H or R;
X$_{12}$ is R, G, or K; and
Z$_1$ to Z$_3$ are each independently A, D, E, G, H, I, L, N, Q, R, S, T, V, or Y.

More preferred are polypeptides that are characterized by binding to a protein containing an Fc region of an immunoglobulin and also by having at least 90% sequence identity to one of the following amino acid sequences:

(SEQ ID No: 1)
ADNRFNREQQNAFYEILHLPNLTEEQRNAFIQSLRDDPSVSREILAEAR

RLNDAQAPG
and

-continued (SEQ ID No: 2)
ADNRFNREQQNAFYEILHLPNLTEEQRNAFIQSLRDDPSVSREILAEAR
RLNDAQAPR.

The sequence identity is more preferably at least 95%, and particularly preferably at least 98%. Polypeptides containing at least 80%, preferably at least 90%, of the sequence (range) of the polypeptides of the present invention are also included in the scope of the present invention even if they are shorter than the polypeptides of the present invention.

The polypeptides also encompass polypeptides containing two or more connected amino acid sequences described above. The lower limit of the number of connected amino acid sequences is at least 2, preferably at least 3, more preferably at least 4, and still more preferably at least 5, and the upper limit thereof is at most 20, preferably at most 10, more preferably at most 8, and still more preferably at most 6. Such multimers may be homopolymers (e.g. homodimers, homotrimers) consisting of connected immunoglobulin-binding polypeptides (domains) of the same amino acid sequence, or may be heteropolymers (e.g. heterodimers, heterotrimers) consisting of connected immunoglobulin-binding polypeptides having different amino acid sequences.

Such polypeptides may be connected without any linker amino acid residues or through one or more linker amino acid residues, but the connection is not limited only to these manners. The number of linker amino acid residues is not limited at all, and the connection is preferably performed without destabilizing the three-dimensional structure of the polypeptides.

The polypeptides of the present invention also encompass fusion proteins in which an immunoglobulin-binding polypeptide or two or more connected immunoglobulin-binding polypeptides, as one component, is/are fused with another protein having a different function. Examples of such fusion proteins include, but are not limited to, fusion proteins with albumin or GST (glutathione S-transferase). Additionally, fusion proteins with a nucleic acid (e.g. a DNA aptamer), a drug (e.g. an antibiotic) or a polymer (e.g. PEG (polyethylene glycol)) are also applicable.

The polypeptides of the present invention are characterized by their high chemical stability under alkali conditions. The term "alkali conditions" refers to levels of alkalinity which are high enough for washing or sterilization purpose. More specifically, the alkali conditions may correspond to, but not limited to, an about 0.05 to 1.0 N sodium hydroxide aqueous solution, for example. The "chemical stability" indicates the ability of a polypeptide to maintain its functions without undergoing chemical modification such as chemical changes of amino acid residues and chemical denaturation such as transfer or cleavage of an amide bond. The "ability of a polypeptide to maintain its functions" herein refers to an ability to maintain the binding activity to the Fc region of an immunoglobulin (the proportion of polypeptide molecules maintaining the affinity without undergoing chemical denaturation). A higher level of "chemical stability" corresponds to a smaller reduction of the binding activity to the Fc region of an immunoglobulin after immersion in an alkaline solution. The phrase "alkali resistance" herein is synonymous with the phrase "chemical stability under alkali conditions".

The affinity for a protein containing an Fc region of an immunoglobulin may be tested by, but not limited to, a biosensor such as a Biacore system (GE Healthcare, Japan) based on the surface plasmon resonance principle. The measurement conditions may be appropriately determined such that a binding signal of the polypeptide of the present invention binding to the Fc region of an immunoglobulin can be detected. Specifically, the affinity can be easily evaluated at a temperature of 20° C. to 40° C. (constant temperature) and a neutral pH of 6 to 8.

Examples of binding parameters include the affinity constant ($K_A$) and the dissociation constant ($K_D$) (Nagata et al., "Real-time analysis of biomolecular interactions", Springer-Verlag Tokyo, 1998, p. 41). The affinity constants of the polypeptides of the present invention for the Fc region of an immunoglobulin may be determined with a Biacore system. Specifically, human IgG is immobilized on a sensor chip in the experimental system, and each domain variant is added to a flow channel at a temperature of 25° C. and a pH of 7.4. The proteins of the present invention preferably have an affinity constant ($K_A$) for human IgG of not less than $1 \times 10^5$ ($M^{-1}$), more preferably not less than $1 \times 10^6$ ($M^{-1}$), and still more preferably $1 \times 10^7$ ($M^{-1}$).

However, when the remaining binding activity after an alkali treatment is determined, the constants $K_A$ and $K_D$ are inappropriate as binding parameters because the binding ability of a protein molecule to an immunoglobulin is not changed by a chemical treatment. A preferred, non-limiting example of methods for determining the remaining binding activity of a protein after an alkali treatment is that where a protein is immobilized on a sensor chip, and then the same concentration of an immunoglobulin is added thereto before and after the chemical treatment of the protein, to determine the magnitude of a binding signal or the theoretical maximum binding capacity (Rmax), which are used as binding parameters. Alternatively, for example, the remaining binding activity may be determined by adding a protein before and after a chemical treatment into an experimental system in which an immunoglobulin is immobilized.

The chemical stability under alkali conditions may be determined not only on the basis of the binding activity to an immunoglobulin, but also on the basis of the stability of a polypeptide itself as an indicator. The chemical stability under alkali conditions can be evaluated, for example, by comparing electrophoresis bands of a polypeptide before and after an alkali treatment, in electrophoresis. More specifically, comparison of the chemical stability can be performed by performing general SDS-PAGE and analyzing bands for intensity via densitometry. When the chemical stability is determined based on the band intensity analyzed via densitometry, the polypeptides of the present invention preferably have a band intensity measured after being left in a 0.5 M sodium hydroxide aqueous solution at 25° C. for 24 hours of not less than 50%, more preferably not less than 60%, still more preferably not less than 70%, and particularly preferably not less than 80%, of that measured before the treatment. When the chemical stability is determined based on the band intensity analyzed via densitometry, the polypeptides of the present invention also preferably have a band intensity measured after being left in a 0.5 M sodium hydroxide aqueous solution at 25° C. for 30 hours of not less than 30%, more preferably not less than 40%, and still more preferably not less than 50%, of that measured before the treatment.

The proteins of the present invention can be produced by inserting DNAs encoding the amino acid sequences of these proteins into vectors, and culturing transformants containing the resulting vectors.

The DNAs may be any DNAs whose base sequences can be translated into amino acid sequences forming the proteins. Such DNAs can be obtained by common known techniques, for example, by using polymerase chain reaction (hereinafter, abbreviated as PCR). Alternatively, the DNAs can be synthesized by known chemical synthesis techniques, or are available from DNA libraries. A codon(s) in the base sequences of these DNAs may be replaced with a degenerate codon(s), in other words, their base sequences are not required to be the same as the original base sequences, as long as the translated proteins are the same as those encoded by the original base sequences.

Site-directed mutagenesis for modifying the base sequences of the DNAs can be carried out using recombinant DNA technology, PCR technology, or the like. Specifically, mutagenesis by recombinant DNA technology can be performed as follows. For example, in the case where there are suitable restriction enzyme recognition sequences on both sides of a mutagenesis target site in the gene encoding the protein of the present invention, cassette mutagenesis can be used in which a region containing the mutagenesis target site is removed by cleaving these restriction enzyme recognition sequences with the restriction enzymes, and then a DNA fragment containing a mutation only at the target site, prepared by chemical synthesis or the like, is inserted therein. Site-directed mutagenesis by PCR can be performed by, for example, double primer mutagenesis in which PCR is carried out using a double-stranded plasmid encoding a protein as a template, and two kinds of synthetic oligo primers containing mutation, complementary to the + and − strands.

Also, a DNA encoding a multimeric protein can be prepared by ligating a desired number of DNAs each encoding a monomeric protein (single domain) of the present invention in tandem. Ligation to prepare a DNA encoding a multimeric protein can be accomplished, for example, by introducing suitable restriction enzyme sites into DNA sequences, fragmenting the DNA sequences with the restriction enzyme, and ligating the obtained double-stranded DNA fragments using a DNA ligase. Only one kind of restriction enzyme site may be introduced, or different kinds of restriction enzyme sites may be introduced.

If the base sequences each encoding a monomeric protein in the DNA encoding a multimeric protein are the same, homologous recombination may occur when the DNA is transformed into host cells. To avoid this, the ligated DNAs each encoding a monomeric protein preferably have 90% or lower base sequence identity, and more preferably 85% or lower base sequence identity to one another.

The aforementioned vectors contain a base sequence encoding the protein described above or a partial amino acid sequence thereof and a promoter that is operably ligated to the base sequence to function in host cells. Typically, these vectors can be constructed by ligating or inserting a gene encoding the protein into a suitable vector. The vector to which the gene is to be inserted is not limited at all, as long as it is capable of autonomous replication in host cells. The vector may be a plasmid DNA or a phage DNA. In the case of using, for example, *Escherichia coli* host cells, examples of the vector include pQE series vectors (QIAGEN), pET series vectors (Merck), and pGEX series vectors (GE Healthcare, Japan). Examples of plasmid vectors useful for gene expression in *Brevibacillus* cells include the known *Bacillus subtilis* vector pUB110, and pHY500 (JP H02-31682 A), pNY700 (JP H04-278091 A), pNU211R2L5 (JP H07-170984 A), and pHT210 (JP H06-133782 A), and the shuttle vector pNCMO2 for *Escherichia coli* and bacteria of *Brevibacillus* (JP 2002-238569 A).

The proteins of the present invention can be prepared as fusion proteins with a protein that is known to help expression of proteins or facilitate purification of proteins. Examples of such proteins include, but are not limited to, maltose-binding protein (MBP) and glutathione S-transferase (GST). Fusion proteins can be produced using a vector in which a DNA encoding the amino acid sequence of the protein of the present invention and a DNA encoding MBP, GST, or the like are ligated together.

The transformants can be obtained by transfection of a vector into host cells. Examples of methods for transfecting a vector into host cells include, but are not limited to, a method using calcium ions, an electroporation method, a spheroplast method, a lithium acetate method, an *Agrobacterium* infection method, a particle gun method, and a polyethylene glycol method. Moreover, in order for the resulting genes to express their function in host cells, for example, a method including incorporation of a gene obtained in the present invention into the genome (chromosome) may also be used.

The host cells are not limited at all, and preferred examples of those suited for low-cost mass production include *Escherichia coli*, *Bacillus subtilis* and bacteria (eubacteria) of genera including *Brevibacillus*, *Staphylococcus*, *Streptococcus*, *Streptomyces*, and *Corynebacterium*.

The proteins of the present invention can be obtained by culturing the transformant cells in a medium to produce and accumulate a protein of the present invention in the cultured cells (including the periplasmic space thereof) or in the liquid culture (extracellularly), and collecting the target protein from the culture.

Alternatively, the proteins of the present invention can be obtained by culturing the transformant cells in a medium to produce and accumulate a fusion protein containing a protein of the present invention in the cultured cells (including the periplasmic space thereof) or in the liquid culture (extracellularly), collecting the fusion protein from the culture, cleaving the fusion protein with an appropriate protease, and collecting the target protein.

The transformant cells can be cultured according to a common method for culturing host cells. The medium to be used for culturing is not limited at all, as long as it allows high-yield, high-efficiency production of the proteins. Specifically, carbon and nitrogen sources such as glucose, sucrose, glycerol, polypeptone, meat extracts, yeast extracts, and casamino acids may be used. In addition, the medium may be supplemented, as required, with inorganic salts such as potassium salts, sodium salts, phosphates, magnesium salts, manganese salts, zinc salts, and iron salts. In the case of auxotrophic host cells, nutritional substances necessary for their growth should be added to the medium. Moreover, antibiotics such as penicillin, erythromycin, chloramphenicol, and neomycin may optionally be added.

Furthermore, a variety of known protease inhibitors, i.e. phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, ethylenediaminetetraacetic acid (EDTA), and/or other commercially available protease inhibitors may be added at appropriate concentrations in order to inhibit degradation or molecular-size reduction of the target proteins by a host-derived protease present inside or outside the cells.

In order to assist accurate folding of the proteins of the present invention, a molecular chaperone such as GroEL/ES, Hsp70/DnaK, Hsp90 and Hsp104/ClpB may be used (for example, such a molecular chaperone may be coexpressed with the protein of the present invention or may be allowed to coexist with the protein of the present invention by combining them into a fusion protein or the like.) Further examples of techniques for accurate folding of the proteins of the present invention include, but are not limited to, addition of an additive for assisting accurate folding to the medium; and culturing at low temperatures.

Examples of media for culturing the transformants of *Escherichia coli* host cells include LB medium (1% triptone, 0.5% yeast extract, 1% NaCl) and 2×YT medium (1.6% triptone, 1.0% yeast extract, 0.5% NaCl).

Examples of media for culturing the transformants of *Brevibacillus* host cells include TM medium (1% peptone, 0.5% meat extract, 0.2% yeast extract, 1% glucose, pH 7.0) and 2SL medium (4% peptone, 0.5% yeast extract, 2% glucose, pH 7.2).

The proteins of the present invention can be accumulated in the cultured cells (including the periplasmic space thereof) or in the liquid culture (extracellularly) by aerobically culturing the cells at a temperature of 15° C. to 42° C., preferably 20° C. to 37° C., for several hours to several days in an aeration-stirring condition, followed by recovering the proteins. Optionally, the cells may be cultured anaerobically without aeration.

In the case where a recombinant protein is produced and secreted, the produced recombinant protein can be recovered, after culturing the cells, by separating the cultured cells from the supernatant containing the secreted protein by a common separation method such as centrifugation and filtration.

Also in the case where the protein is produced and accumulated in the cultured cells (including the periplasmic space thereof), the protein accumulated in the cells can be recovered, for example, by collecting the cells from the liquid culture by centrifugation, filtration or the like, and then disrupting the cells by sonication, a French press treatment or the like, and/or adding an agent for making the protein soluble, such as a surfactant.

Purification of the proteins of the present invention can be performed by any one or an appropriate combination of techniques such as affinity chromatography, cation or anion exchange chromatography and gel filtration chromatography.

Examples of techniques to confirm whether the purified product is a target protein include common techniques such as SDS polyacrylamide gel electrophoresis, N-terminal amino acid sequence analysis, and Western blot analysis.

The proteins of the present invention can also be produced using a cell-free protein synthesis system with the DNA described above. Examples of such cell-free protein synthesis systems include synthesis systems derived from procaryotes, plant cells, and higher animal cells.

The proteins of the present invention can be used as affinity ligands characteristically having affinity for an immunoglobulin, and affinity separation matrices can be obtained by immobilizing the ligands to carriers made of a water-insoluble base material.

The term "affinity ligand" refers to a substance (functional group) that selectively captures (binds to) a target molecule in a mixture of molecules due to a specific affinity between molecules, typically, antigen-antibody binding affinity, and refers herein to a protein that specifically binds to an immunoglobulin. The term "ligand" as used alone herein is synonymous with the "affinity ligand".

Examples of carriers made of a water-insoluble base material used for immobilization of the affinity ligands include inorganic carriers such as glass beads and silica gel; organic carriers such as synthetic polymers (e.g. cross-linked polyvinyl alcohol, cross-linked polyacrylate, cross-linked polyacrylamide, cross-linked polystyrene) and polysaccharides (e.g. crystalline cellulose, cross-linked cellulose, cross-linked agarose, cross-linked dextran); and composite carriers of combinations of these carriers, such as organic-organic or organic-inorganic composite carriers. Examples of commercial products thereof include GCL2000 (porous cellulose gel), Sephacryl S-1000 (prepared by covalently cross-linking allyl dextran with methylenebisacrylamide), Toyopearl (methacrylate carrier), Sepharose CL4B (cross-linked agarose carrier), and Cellufine (cross-linked cellulose carrier). It should be noted that the carriers listed above do not limit the range of water-insoluble carriers usable in the present invention.

Considering the purpose and manner of use of the affinity separation matrices, the water-insoluble carrier desirably has a large surface area, and is preferably a porous matrix having a large number of fine pores of a suitable size. The carrier may be in any form such as beads, monolith, fiber, or film (including hollow fiber), and any form can be selected appropriately.

Immobilization of the ligands may be performed, for example, by conventional coupling methods utilizing amino, carboxyl or thiol groups of the ligands to couple the ligands with the carriers. Examples of such coupling methods include immobilization methods including reacting the carrier with cyanogen bromide, epichlorohydrin, diglycidyl ether, tosyl chloride, tresyl chloride, hydrazine, sodium periodate, or the like to activate the carrier (or introducing a reactive functional group to the carrier surface), followed by a coupling reaction between the carrier and a compound to be immobilized as the ligand; and immobilization methods including adding a condensation reagent (e.g. carbodiimide) or a reagent containing a plurality of functional groups in the molecule (e.g. glutaraldehyde) to a system containing the carrier and a compound to be immobilized as the ligand, followed by condensation and crosslinking. A spacer molecule consisting of a plurality of atoms may also be introduced between the ligand and the carrier, or alternatively, the ligand may be directly immobilized on the carrier. In this case, for immobilization, the proteins of the present invention may be chemically modified, or may incorporate an amino acid residue useful for immobilization. Examples of amino acid residues useful for immobilization include amino acid residues containing a functional group useful for a chemical reaction for immobilization in a side chain, such as Lys which contains an amino group in a side chain, and Cys which contains a thiol group in a side chain. The proteins of the present invention may be modified or altered in any manner for immobilization, as long as matrices with the proteins immobilized as ligands still maintain the effects of the proteins of the present invention.

More specifically, the ligands may preferably be covalently immobilized on the carrier via the ε-amino group of lysine residue(s) of the ligands by a conventional coupling method. It is preferable that the polypeptides without Lys, among the proteins of the present invention, be modified to incorporate an additional sequence with Lys useful for immobilization as described above. Such an additional sequence with Lys is preferably added to an end of the polypeptide. The term "additional sequence with Lys" herein refers to a sequence containing at least one Lys residue, and the number of Lys residues is preferably 1 to 10, more preferably 1 to 5, and still more preferably 1 to 3. In the case where a plurality of Lys residues are present, the Lys residues are not required to be consecutive (next to one another). The number of amino acid residues in the additional sequence with Lys located terminally is not limited at all, and the sequence may consist of only one lysine residue. The number of amino acid residues in the additional sequence with Lys is preferably 1 to 20, more preferably 1 to 10, and still more preferably 1 to 5. The expression "added to an end" basically means the addition to the N or C terminal of the amino acid sequence. Thus, Lys residue(s) may be added to the polypeptides of the present invention by mutation of the polypeptides at an end.

The "protein containing an Fc region of an immunoglobulin" refers to a protein containing a site of the Fc region to which the proteins of the present invention can bind, and is not required to contain the entire Fc region.

Such proteins containing an Fc region of an immunoglobulin can be purified according to an affinity column chromatography method using a commercially available column. Specifically, a buffer containing a protein containing an Fc region of an immunoglobulin is adjusted to be neutral and the resulting solution is run through an affinity column filled with the affinity separation matrix to adsorb the protein containing an Fc region of an immunoglobulin to the affinity separation matrix. Next, an adequate amount of a pure buffer is run through the affinity column to wash the inside of the column. At this time, the target protein containing an Fc region of an immunoglobulin remains adsorbed on the affinity separation matrix of the present invention in the column. Subsequently, an acidic buffer adjusted to a proper pH (which may contain a substance for accelerating dissociation of the protein from the matrix) is run through the column to elute the target protein containing an Fc region of an immunoglobulin. Thus, high-level purification can be achieved. The affinity separation matrix can be reused through a washing process in which a pure buffer (in some cases, a solution containing an appropriate modifier or organic solvent) having an appropriately strong acidity or alkalinity which does not completely impair the functions of the ligand compound and the carrier base material is run through the matrix.

EXAMPLES

Example 1

Preparation of Novel Polypeptides

Oligonucleotides respectively having the nucleotide sequences of SEQ ID Nos:3 and 4 were mixed and subjected to overlap PCR using a Blend Taq polymerase (TOYOBO CO., LTD.) in accordance with the attached protocol. The double-stranded DNA PCR product was extracted and purified by agarose electrophoresis, and then cleaved with restriction enzymes BamHI and HindIII (both available from Takara Bio, Inc.). Another double-stranded DNA of interest was obtained by PCR from oligonucleotides respectively having the nucleotide sequences of SEQ ID Nos:5 and 6 in the same manner as described above, and then cleaved with restriction enzymes HindIII and EcoRI (both available from Takara Bio, Inc.).

These two double-stranded DNAs were subcloned into the BamHI/EcoRI site in a multiple cloning site of the plasmid vector pGEX-2T (GE Healthcare, Japan). Specifically, the vector pGEX-2T was cleaved with the restriction enzymes BamHI and EcoRI, dephosphorylated by Alkaline Phosphatase (Takara Bio, Inc.), and then mixed with the two restriction enzyme treated double-stranded DNAs, and they were subjected to a ligation reaction with Ligation High (TOYOBO CO., LTD.) in accordance with the attached protocol. The DNAs of SEQ ID Nos:3, 4, 5, and 6 were designed such that the two double-stranded DNAs, when ligated through the HindIII cleavage sites and subcloned into pGEX-2T, encode SEQ ID No:1. E. coli HB101 cells (Takara Bio, Inc.) were transformed with the pGEX-2T containing the DNA encoding SEQ ID No:1 (the ligation solution), and the plasmid DNA was amplified and extracted by a common method.

(1) PCR was performed using this expression plasmid as a template and oligonucleotide primers of SEQ ID Nos:7 and 8. The PCR product was purified and treated with restriction enzymes PstI and cfr13I (Takara Bio, Inc.) to prepare a double-stranded insert DNA. (2) Another double-stranded insert DNA was prepared by performing PCR using the same template and oligonucleotide primers of SEQ ID Nos:9 and 10, purifying the PCR product, and then treating it with restriction enzymes cfr13I and EcoRI. (3) These two double-stranded insert DNAs were mixed with the *Brevibacillus* expression vector pNK3260' (WO 2006/004067) which had been treated with restriction enzymes PstI and EcoRI and dephosphorylated, and they were subjected to a ligation reaction. In this manner, an expression plasmid containing a DNA encoding a polypeptide with connected amino acid sequences of SEQ ID No.1 was constructed.

At the same time, an expression plasmid containing a DNA encoding a polypeptide with connected amino acid sequences of SEQ ID No:2 was also constructed using oligonucleotide primers of SEQ ID Nos:7 and 11 and restriction enzymes PstI and XhoI (Takara Bio, Inc.) in the process (1) and oligonucleotide primers of SEQ ID Nos:9 and 12 and restriction enzymes XhoI and EcoRI in the process (2). The amino acid residue at the C terminal (the last residue of the second repeat) was replaced with Lys for easy genetic manipulation, and this replacement does not affect the evaluation results because it is at the C terminal.

These expression plasmids were transformed into *Brevibacillus choshinensis* FY-1. The transformation was performed by a known electroporation method ("Biosci. Biotech. Biochem.", 1997, Vol. 61, pp. 202-203). The *Brevibacillus choshinensis* FY-1 is a Phe- and Tyr-requiring strain obtained by mutating *Brevibacillus choshinensis* HPD31-OK (JP H06-296485 A).

The *Brevibacillus choshinensis* FY-1 recombinant cells were cultured with shaking for 3 days at 30° C. in 5 mL of 3YC medium (3% polypeptone, 0.2% yeast extract, 3% glucose, 0.01% magnesium sulfate, 0.001% iron sulfate, 0.001% manganese chloride, 0.0001% zinc chloride) containing 60 µg/mL neomycin.

The culture was centrifuged to remove cells, and the obtained culture supernatant was subjected to cation exchange chromatography using an SP Fast Flow column (GE Healthcare, Japan) to purify the target polypeptide. More specifically, sodium acetate was added to the culture supernatant to a final concentration of 50 mM, and hydrochloric acid was then added to the culture supernatant to adjust the pH to 4.0. Then, the resulting culture supernatant was applied to the SP Fast Flow column equilibrated with a cation exchange buffer A (50 mM $CH_3COOH$—$CH_3COONa$, pH 4.0). After washing the column with the cation exchange buffer A, the target polypeptide was eluted and separated in the process of salt gradient elution with the cation exchange buffer A and a cation exchange buffer B (50 mM $CH_3COOH$—$CH_3COONa$, 1 M NaCl, pH 4.0). Next, the target polypeptide was purified by anion exchange chromatography using a DEAE Fast Flow column (GE Healthcare, Japan). More specifically, the separated target protein solution was dialyzed against ultrapure water, and applied to the DEAE Fast Flow column equilibrated with an anion exchange buffer A (50 mM Tris-HCl, pH 8.0). After washing with the anion exchange buffer A, the target polypeptide was eluted and separated in the process of salt gradient elution with the anion exchange buffer A and an anion exchange buffer B (50 mM Tris-HCl, 0.3 M NaCl, pH 8.0). The separated target polypeptide solution was again dialyzed against ultrapure water. In this manner, an aqueous solution containing only the target polypeptide was obtained as a final purified sample. All the protein purification processes by chromatography using a column were performed with an AKTAprime plus system (GE Healthcare, Japan).

The amino acid sequences of the two polypeptides prepared through the processes described above and used in the following examples are shown as SEQ ID No:13 (two connected sequences of SEQ ID No:1) and SEQ ID No:14 (two connected sequences of SEQ ID No:2).

Example 2

Analysis for Affinity of Polypeptides to Human IgG

The polypeptides obtained in Example 1 were analyzed for affinity for an immunoglobulin with a Biacore 3000 biosensor (GE Healthcare, Japan) based on surface plasmon resonance.

A human immunoglobulin G preparation (hereinafter, referred to as human IgG) separated from human plasma was immobilized on a sensor chip, and each protein was flowed onto the chip to detect an interaction between them. The immobilization of the human IgG onto the sensor chip CM5 was carried out by amine coupling using N-hydroxysuccinimide (NHS) and N-ethyl-N'-(3-dimethylaminopropyl)carbodiimide hydrochloride (EDC), and ethanolamine was used for blocking (both the sensor chip and the immobilization reagents are available from GE Healthcare, Japan). The human IgG solution was prepared by dissolving Gammagard (Baxter) in a standard buffer (20 mM $NaH_2PO_4$—$Na_2HPO_4$, 150 mM NaCl, pH 7.4) to a concentration of 1.0 mg/mL. The human IgG solution was then diluted to 1/100 in an immobilization buffer (10 mM $CH_3COOH$—$CH_3COONa$, pH 4.5). The human IgG was immobilized on the sensor chip in accordance with the protocol attached to the Biacore 3000. A reference cell to be used as a negative control was also prepared by immobilizing ethanolamine in another flow cell on the chip after activation with EDC/NHS.

The polypeptides prepared in the manner described in Example 1 were appropriately prepared at concentrations of 10 to 1000 nM in a running buffer (20 mM $NaH_2PO_4$—$Na_2HPO_4$, 150 mM NaCl, 0.005% P-20, pH 7.4) (solutions of three different protein concentrations were prepared for each polypeptide), and each polypeptide solution was then added to the sensor chip at a flow rate of 20 µL/min for 30 seconds. Binding sensorgrams at 25° C. were continuously recorded during the addition (association phase, 90 seconds) and after the addition (dissociation phase, 90 seconds). After each recording, the sensor chip was regenerated by adding 40 mM NaOH (for 15 seconds). This process was intended to remove the added proteins remaining on the sensor chip, and was found to substantially completely restore the binding activity of the immobilized human IgG. The affinity constant for human IgG ($K_A=k_{on}/k_{off}$) was calculated by performing a fitting analysis on each of the obtained binding sensorgrams (the binding sensorgrams obtained by subtracting the binding sensorgram of the reference cell) using the 1:1 binding model in a BIA evaluation software attached to the system.

The polypeptide of SEQ ID No:13 was found to have an affinity constant ($K_A$) for the polypeptide antibody of SEQ ID No:1 of $2.1\times10^8$ ($M^{-1}$), and the polypeptide of SEQ ID No:14 was found to have an affinity constant ($K_A$) for the polypeptide antibody of SEQ ID No:1 of $2.6\times10^8$ ($M^{-1}$). These results show that these peptides had sufficient affinity for a human immunoglobulin.

Example 3

Evaluation of Stability of Novel Polypeptides Against Alkali by SDS-PAGE Analysis The polypeptides prepared in Example 1 were evaluated by comparing their bands on SDS-PAGE gels obtained after incubation under alkali conditions for a predetermined period.

The alkali treatment was performed as follows. NaOH was added to 200 µM of each of the polypeptides to a final concentration of 0.5 M, and the solutions were incubated at 25° C. for 4, 8, and 24 hours. To the resulting polypeptide solutions, 0.5 M HCl (in a predetermined amount which was previously found to adjust the pH back to neutral) was added to neutralize the solutions. Thus, SDS-PAGE samples were prepared. SDS-PAGE samples before the alkali treatment (0 hour after treatment) were prepared by adding a mixture of the NaOH solution for the alkali treatment and the HCl solution for the neutralization treatment to bring all samples to the same polypeptide concentration and the same solution composition. SDS-PAGE was performed using a mini-slab size electrophoresis bath "pageRun" with power supply and a 15% polyacrylamide precast gel "e-PAGEL" (both available from ATTO CORPORATION) in accordance with the attached manual (common method). The electrophoresis gels were stained and destained, and then electronically imaged using a ChemiDoc XRS imaging system (Bio-Rad Laboratories, Inc.), and the bands were analyzed (via densitometry) with a Quantity One software (Bio-Rad Laboratories, Inc.) attached to the system in accordance with the manual. FIG. 1 shows an electronic image obtained by the SDS-PAGE.

The results of the ratio of the band intensity measured 24 hours after the alkali treatment (the remaining intensity as calculated based on the intensity before the alkali treatment (=100%)) were as follows: the ratio of the known highly alkali-resistant polypeptide (Comparative Example 1, two connected sequences of SEQ ID No:15) was 55.0%, whereas the ratio of the polypeptide of SEQ ID No:13 was 60.9% and the ratio of the polypeptide of SEQ ID No:14 was 91.6%.

Thus, the polypeptides according to the present invention were proven to have high stability under severe alkali conditions. In particular, the polypeptide of SEQ ID No:14 (the sequence derived from SEQ ID No:2) exhibited little change in the band intensity even after 4-hour incubation in 0.5 M NaOH at 25° C. (99.8%), and was thus proven to be practically very valuable in various applications.

Example 4

Preparation of Novel Polypeptides

Quick change mutagenesis was performed using the pGEX-2T containing the DNA encoding SEQ ID No:1 obtained in Example 1 as a template DNA and two primers to provide an expression plasmid containing an additional mutation. The quick change mutagenesis was performed in accordance with the protocol of Stratagene using Pfu Turbo DNA polymerase and the methylated DNA (template DNA) cleavage enzyme DpnI (all available from Stratagene). The following seven primer sets were used to prepare expression plasmids containing an additional mutation: SEQ ID Nos:16 and 17; SEQ ID Nos:18 and 19; SEQ ID Nos:20 and 21; SEQ ID Nos:22 and 23; SEQ ID Nos:24 and 25; SEQ ID Nos:26 and 27; and SEQ ID Nos:28 and 29. Additionally, a further mutated expression plasmid was prepared using the primers of SEQ ID Nos:18 and 19 and the expression plasmid that had been prepared using the primers of SEQ ID Nos:16 and 17 as a template DNA. Thus, eight new expression plasmids were prepared.

The processes (1) to (3) of Example 1 were performed using these expression plasmids as templates to provide four expression plasmids containing a DNA encoding a polypeptide having an amino acid sequence consisting of repeats of the same sequence (each of the following amino acid sequences of SEQ ID Nos:30 to 37).

ADNRFNREQQNAFYEILHLPNLTEEQRNAFIQSLRDDPSVSREILAEAQ
RLNDAQAPR (SEQ ID No: 30)

ADNRFNREQQNAFYEILHLPNLTEEQRNAFIQSLIDDPSVSREILAEAQ
RLNDAQAPR (SEQ ID No: 31)

ADNRFNREQQNAFYEILHLPNLTEEQRNAFIQSLIDDPSVSREILAEAR
RLNDAQAPR (SEQ ID No: 32)

ADNRFNREQQNAFYEILHLPNLTEEQRNAFIQSLHDDPSVSREILAEAR
RLNDAQAPR (SEQ ID No: 33)

ADNRFNREQQNAFYEILHLPNLTEEQRNAFIQELRDDPSVSREILAEAR
RLNDAQAPR (SEQ ID No: 34)

ADNRFNREQQNAFYEILHLPNLTEEQRNAFIQLLRDDPSVSREILAEAR
RLNDAQAPR (SEQ ID No: 35)

DNRFNREQQNAFYEILHLPNLTEEQRNAFIQTLRDDPSVSREILAEARR
LNDAQAPR A(SEQ ID No: 36)

ADNRFNREQQNAFYEILHLPNLTEEQRNAFIQSLRIDPSVSREILAEAR
RLNDAQAPR (SEQ ID No: 37)

The amino acid sequences of these polypeptides are shown as SEQ ID Nos:38 to 45. The amino acid residue at the C terminal (the last residue of the second repeat) was replaced with Lys as described in Example 1, and this replacement does not affect the evaluation results because it is at the C terminal.

These expression plasmids were used to express and purify polypeptides in the same manner as in Example 1.

Example 5

Evaluation of Stability of Novel Polypeptides Against Alkali by SDS-PAGE Analysis The polypeptides prepared in Example 4 were evaluated by comparing their bands on SDS-PAGE gels obtained after incubation under alkali conditions for a predetermined period in the same manner as in Example 3. The polypeptides of SEQ ID Nos:38 to 41 were evaluated for stability after 4-hour and 24-hour incubation. The polypeptides of SEQ ID Nos:42 to 45 were evaluated for stability after 30-hour incubation. As a reference, the polypeptide of SEQ ID No:14 was also subjected to the same processes.

Figure 2:
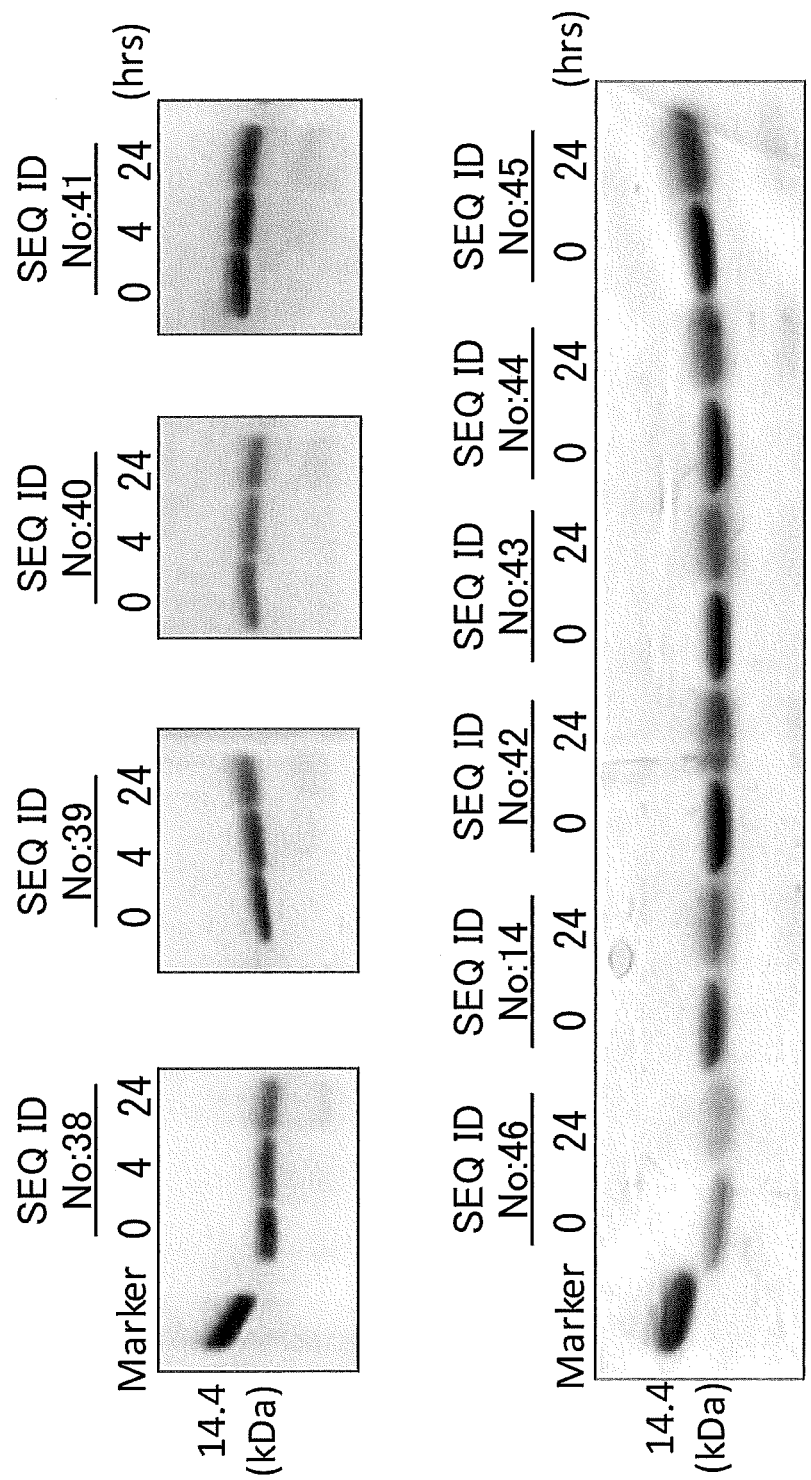
FIG. 2 shows the results of Example 5 and Comparative Example 2, specifically the results of SDS-PAGE on polypeptides of SEQ ID Nos:38 to 46 after exposed to an alkali treatment (for 0, 4, and 24 hours).

FIG. 2 shows electronic images obtained by the SDS-PAGE. The results of the ratio of the band intensity measured 24 hours after the alkali treatment were as follows: the ratio of the polypeptide of SEQ ID No:38 was 73.4%; the ratio of the polypeptide of SEQ ID No:39 was 79.0%; the ratio of the polypeptide of SEQ ID No:40 was 85.6%; and the ratio of the polypeptide of SEQ ID No:41 was 82.8%. Also, the results of the ratio of the band intensity measured 30 hours after the alkali treatment were as follows: the ratio of the known alkali-resistant polypeptide (Comparative Example 2, two connected sequences of SEQ ID No:46) was 23.1%, whereas the ratio of the polypeptide of SEQ ID No:14 was 45.1%, the ratio of the polypeptide of SEQ ID No:42 was 45.8%, the ratio of the polypeptide of SEQ ID No:43 was 43.8%, the ratio of the polypeptide of SEQ ID No:44 was 49.6%, and the ratio of the polypeptide of SEQ ID No:45 was 65.0%. Thus, these polypeptides were also proven to have high stability under severe alkali conditions.

Comparative Example 1

Preparation and Evaluation of C-G29A.2d

C-G29A.2d is a functionally equivalent variant of the C domain of Protein A which contains the mutation G29A, and this polypeptide is known to have very high alkali resistance (Patent Literature 5). A DNA encoding a polypeptide (SEQ ID No:15) consisting of tandem repeats of the functionally equivalent variant was subjected to PCR to amplify a product that can be cleaved at the PstI/EcoRI sites, and the amplified product was subcloned into the vector pNK3260'. The expression and purification were performed in the same manner as in Example 1, and the evaluation for alkali resistance was performed in the same manner as in Example 3.

Comparative Example 2

Preparation and Evaluation of C-G29A/S33E.2d

A polypeptide obtained by introducing the mutation S33E into C-G29A is known to have equivalent alkali resistance to that of C-G29A (WO 2011/118699). A polypeptide (SEQ ID No:46) consisting of tandem repeats of the sequence thereof was expressed and purified in the same manner as in Example 1, and evaluated for alkali resistance in the same manner an in Example 3.

The invention claimed is:

1. A polypeptide, that binds to a protein comprising an Fc region of an immunoglobulin, the polypeptide comprising the following amino acid sequence:

(SEQ ID NO: 47)
RFX$_1$X$_2$EQQNAFYEILHX$_3$PNLTEEQRNX$_4$FIQX$_5$LX$_6$X$_7$X$_8$PSVSREX$_9$LAEAX$_{10}$X$_{11}$LNDAQAPX$_{12}$ wherein X$_1$ is D, E, N, or Q;
X$_2$ is E or R;
X$_3$ is L, M, or I;
X$_4$ is A, E, F, R, Y, or W;
X$_5$ is D, E, H, I, L, Q, R, S, T, or V;
X$_6$ is H, I, or R;
X$_7$ is D, I, or R;
X$_8$ is D or E;
X$_9$ is I, L, or V;
X$_{10}$ is R or Q;
X$_{11}$ is H or R; and
X$_{12}$ is R, G, or K.

2. A polypeptide, that binds to a protein comprising an Fc region of an immunoglobulin, the polypeptide comprising the following amino acid sequence:

(SEQ ID NO: 48)
Z$_1$Z$_2$Z$_3$RFX$_1$X$_2$EQQNAFYEILHX$_3$PNLTEEQRNX$_4$FIQX$_5$LX$_6$X$_7$X$_8$PSVSREX$_9$LAEAX$_{10}$X$_{11}$LNDAQAPX$_{12}$ wherein X$_1$ is D, E, N, or Q;
X$_2$ is E or R;
X$_3$ is L, M, or I;
X$_4$ is A, E, F, R, Y, or W;
X$_5$ is D, E, H, I, L, Q, R, S, T, or V;
X$_6$ is H, I, or R;
X$_7$ is D, I, or R;
X$_8$ is D or E;
X$_9$ is I, L, or V;
X$_{10}$ is R or Q;
X$_{11}$ is H or R;
X$_{12}$ is R, G, or K; and
Z$_1$ to Z$_3$ are each independently A, D, E, G, H, I, L, N, Q, R, S, T, V, or Y.

3. The polypeptide according to claim 1,
which has at least 90% sequence identity to one of the following amino acid sequences:

(SEQ ID No: 1)
ADNRFNREQQNAFYEILHLPNLTEEQRNAFIQSLRDDPSVSREILAEAR
RLNDAQAPG and (SEQ ID No: 2)
ADNRFNREQQNAFYEILHLPNLTEEQRNAFIQSLRDDPSVSREILAEAR
RLNDAQAPR.

4. The polypeptide according to claim 2,
which has at least 90% sequence identity to one of the following amino acid sequences:

(SEQ ID No: 1)
ADNRFNREQQNAFYEILHLPNLTEEQRNAFIQSLRDDPSVSREILAEAR
RLNDAQAPG and (SEQ ID No: 2)
ADNRFNREQQNAFYEILHLPNLTEEQRNAFIQSLRDDPSVSREILAEAR
RLNDAQAPR.

* * * * *